United States Patent
Yoo et al.

(10) Patent No.: US 9,042,981 B2
(45) Date of Patent: May 26, 2015

(54) VAGUS NERVE STIMULATION WITH TARGET EFFECTS CONTROLLED BY ADJUSTING TEMPORAL PARAMETERS

(75) Inventors: Paul B. Yoo, Raleigh, NC (US); Warren M. Grill, Chapel Hill, NC (US); Juan Gabriel Hincapie Ordonez, Maple Grove, MN (US)

(73) Assignees: Cardiac Pacemakers, Inc., St. Paul, MN (US); Duke University, Durham, NC (US)

( * ) Notice: Subject to any disclaimer, the term of this patent is extended or adjusted under 35 U.S.C. 154(b) by 225 days.

(21) Appl. No.: 13/114,686

(22) Filed: May 24, 2011

(65) Prior Publication Data

US 2011/0301659 A1  Dec. 8, 2011

Related U.S. Application Data

(60) Provisional application No. 61/351,186, filed on Jun. 3, 2010.

(51) Int. Cl.
*A61N 1/00* (2006.01)
*A61N 1/36* (2006.01)
*A61B 5/00* (2006.01)
*A61N 1/18* (2006.01)

(52) U.S. Cl.
CPC .............. *A61N 1/36139* (2013.01); *A61N 1/18* (2013.01); *A61N 1/36* (2013.01); *A61B 5/4035* (2013.01); *A61N 1/36114* (2013.01); *A61N 1/36117* (2013.01)

(58) Field of Classification Search
None
See application file for complete search history.

(56) References Cited

U.S. PATENT DOCUMENTS

| | | | |
|---|---|---|---|
| 6,104,956 A | 8/2000 | Naritoku et al. | |
| 6,466,822 B1 | 10/2002 | Pless | |
| 6,556,868 B2 | 4/2003 | Naritoku et al. | |
| 7,444,184 B2 * | 10/2008 | Boveja et al. | 607/40 |
| 7,783,362 B2 * | 8/2010 | Whitehurst et al. | 607/116 |
| 2002/0072776 A1 | 6/2002 | Osorio et al. | |
| 2005/0137645 A1 | 6/2005 | Voipio et al. | |
| 2006/0116737 A1 | 6/2006 | Libbus | |
| 2006/0271108 A1 | 11/2006 | Libbus et al. | |
| 2008/0051839 A1 | 2/2008 | Libbus et al. | |
| 2008/0058873 A1 | 3/2008 | Lee et al. | |
| 2008/0058874 A1 | 3/2008 | Westlund et al. | |

(Continued)

FOREIGN PATENT DOCUMENTS

WO  WO-2011153027 A1  12/2011

OTHER PUBLICATIONS

"International Application Serial No. PCT/US2011/037738, International Preliminary Report on Patentability mailed Dec. 13, 2012", 9 pgs.

(Continued)

*Primary Examiner* — Christopher D Koharski
*Assistant Examiner* — Elizabeth K So
(74) *Attorney, Agent, or Firm* — Schwegman Lundberg & Woessner, P.A.

(57) ABSTRACT

One or more temporal stimulation parameters of vagus nerve stimulation (VNS) are selected to substantially modulate one or more target physiological functions without substantially modulating one or more non-target physiological functions. In one embodiment, a stimulation duty cycle is selected such that VNS is delivered to the cervical vagus nerve trunk to modulate a cardiovascular function without causing laryngeal muscle contractions.

19 Claims, 5 Drawing Sheets

(56) References Cited

U.S. PATENT DOCUMENTS

2008/0058892 A1 3/2008 Haefner et al.
2008/0234780 A1 9/2008 Smith et al.
2010/0010556 A1 1/2010 Zhao et al.

OTHER PUBLICATIONS

"International Application Serial No. PCT/US2011/037738, International Search Report mailed Sep. 15, 2011", 5 pgs.

"International Application Serial No. PCT/US2011/037738, Written Opinion mailed Sep. 15, 2011", 8 pgs.

"Australian Application Serial No. 2011261702, Subsequent Examiners Report mailed Nov. 13, 2013", 3 pgs.

"European Application Serial No. 11723161.3, Examination Notification Art. 94(3) mailed Oct. 4, 2013", 7 pgs.

"Australian Application Serial No. 2011261702, Response filed Oct. 31, 2013 to Subsequent Examiners Report mailed Nov. 13, 2013", 21 pgs.

"Australian Application Serial No. 2011261702, Third Examiners Report mailed May 27, 2014", 4 pgs.

"European Application Serial No. 11723161.3, Examination Notification Art. 94(3) mailed Mar. 12, 2014", 7 pgs.

"European Application Serial No. 11723161.3, Response filed Feb. 4, 2014 to Examination Notification Art. 94(3) mailed Oct. 4, 2013", 8 pgs.

\* cited by examiner

# VAGUS NERVE STIMULATION WITH TARGET EFFECTS CONTROLLED BY ADJUSTING TEMPORAL PARAMETERS

CLAIM OF PRIORITY

This application claims the benefit of priority under 35 U.S.C. §119(e) of U.S. Provisional Patent Application Ser. No. 61/351,186, filed on Jun. 3, 2010, which is herein incorporated by reference in its entirety.

TECHNICAL FIELD

This document relates generally to neurostimulation and more particularly to vagus nerve stimulation (VNS) with one or more temporal parameters selected to modulate one or more target physiological functions without substantially modulating one or more non-target physiological functions.

BACKGROUND

Vagus nerve stimulation (VNS) has been applied to modulate various physiologic functions and treat various diseases. One example is the modulation of cardiac functions in a patient suffering heart failure or myocardial infarction. The myocardium is innervated with sympathetic and parasympathetic nerves including the cardiac branches of the vagus nerve. Activities in the vagus nerve, including artificially applied electrical stimuli, modulate the heart rate and contractility (strength of the myocardial contractions). Electrical stimulation applied to the vagus nerve is known to decrease the heart rate and the contractility, lengthening the systolic phase of a cardiac cycle, and shortening the diastolic phase of the cardiac cycle. This ability of VNS is utilized, for example, to control myocardial remodeling.

In addition to treating cardiac disorders such as myocardial remodeling, VNS is also know to be effective in treating disorders including, but not limited to, depression, anorexia nervosa/eating disorders, pancreatic function, epilepsy, hypertension, inflammatory disease, and diabetes. Because many physiological functions are controlled or affected by the neural activities in the vagus nerve, there is a need to control VNS for the desirable functional outcome while minimizing side effects.

SUMMARY

One or more temporal stimulation parameters of vagus nerve stimulation (VNS) are selected to substantially modulate one or more target physiological functions without substantially modulating one or more non-target physiological functions. The one or more temporal parameters specify timing of the electrical stimulation pulses.

In one embodiment, electrical stimulation pulses are delivered to a vagus nerve. The delivery of the electrical stimulation pulses is controlled using one or more temporal parameters selected to result in substantial change in a first physiological function without substantial change in a second physiological function. The first and second physiological functions are each adjustable by the electrical stimulation pulses delivered to the vagus nerve.

In one embodiment, electrical stimulation pulses are delivered to a vagus nerve. The delivery of the electrical stimulation pulses is controlled using a temporal parameter selected to modulate a cardiovascular function without causing contraction of a laryngeal muscle.

In one embodiment, a system for electrically stimulating a vagus nerve includes a stimulation circuit and a stimulation control circuit. The stimulation circuit delivers electrical stimulation pulses to the vagus nerve. The stimulation control circuit controls the delivery of the electrical stimulation pulses using a plurality of stimulation parameters. The stimulation control circuit includes a storage circuit storing the plurality of stimulation parameters including at least a stimulation parameter selected for the delivery of the electrical stimulation pulses to modulate a cardiovascular function without causing contraction of a laryngeal muscle.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
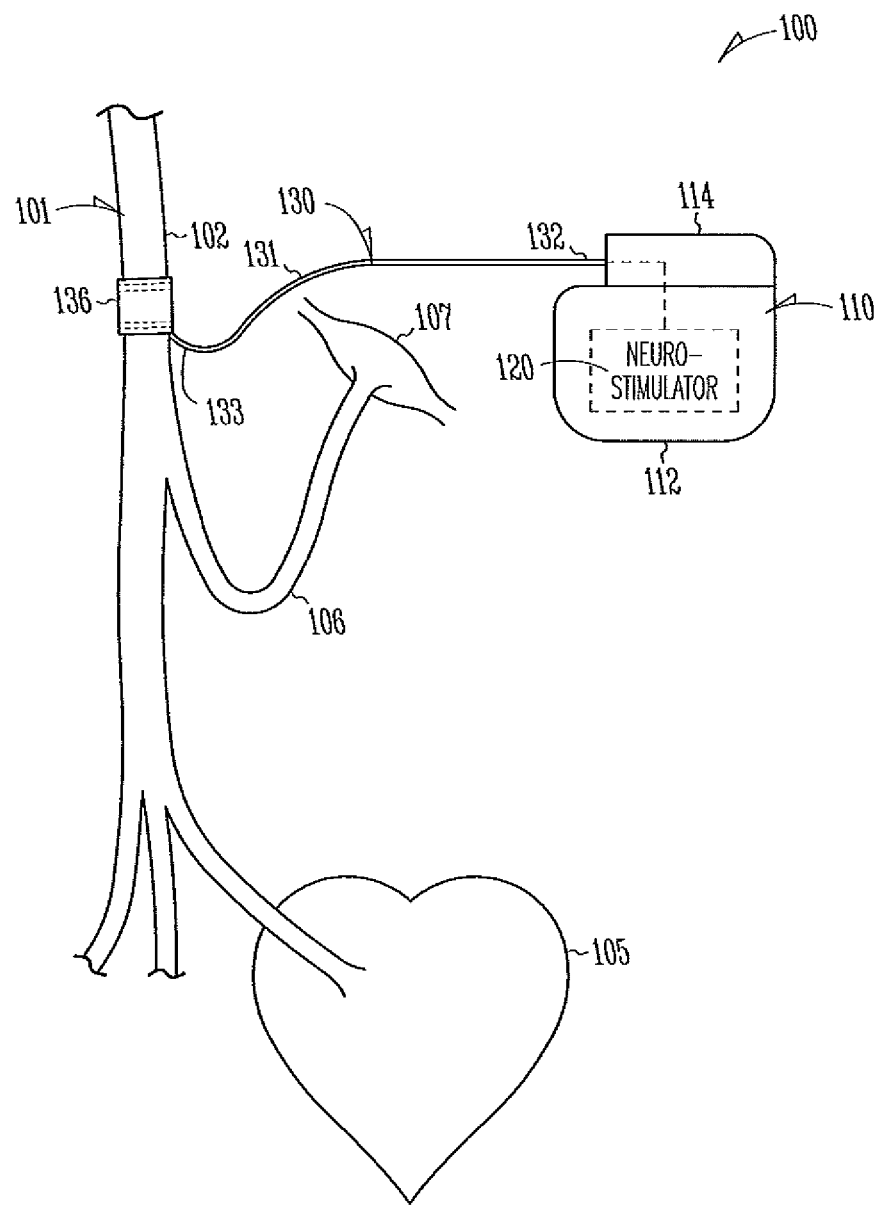
FIG. 1 is an illustration of an embodiment of a vagus nerve stimulation (VNS) system and portions of an environment in which the VNS system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a method and system for stimulating the vagus nerve to modulate one or more target physiological functions while minimizing stimulation-evoked side effects. Vagus nerve stimulation (VNS) has been used for the treatment of neurological disorders including depression and epilepsy. VNS is also investigated for treatment of various disorders such as Alzheimer's disease, anxiety, heart failure, and obesity.

The vagus nerve originates in the medulla and targets multiple organs in a person's body through a complex functional innervation pattern. There are both efferent and afferent nerve fibers within the vagus nerve trunk that convey neural activity to and from visceral organs such as the esophagus, gastrointestinal tract, kidney and pancreas (abdominal branch of vagus), thoracic organs such as the heart and lungs (thoracic branch of vagus), and voluntary muscles of the neck and multiple segments of the upper airway (recurrent laryngeal nerve, RLN). Such complexity has been significantly limiting the effectiveness of VNS and the overall patient population that could benefit from this therapy.

The difficulty in therapeutic application of VNS is further complicated by the total number of fibers within the vagus nerve trunk and the distribution of nerve fibers having different diameter. In an adult dog, which has been used as an animal model for the human vagus nerve, the cervical vagus nerve trunk contains approximately 20,000 myelinated neurons and an even greater number of unmyelinated neurons. Both the human and canine vagus nerves also share a common classification scheme defined by the diameter of nerve fibers. This is based on the classical designation of A (myelinated), B (myelinated parasympathetic) and C (unmyelinated) type fibers, as summarized in Table 1.

TABLE 1

Summary of Vagus Nerve Fiber Type Properties.

|  | A-Fibers | B-Fibers | C-Fibers |
| --- | --- | --- | --- |
| Diameter (μm) | 5-20 | 1-3 | 0.2-2 |
| Myelinated | Yes | Yes | No |
| Conduction Velocity (m/s) | 30-120 | 3-20 | 0.3-2 |
| Per-Unit Latencies (ms/cm) | 0.08-0.3 | 0.5-3.3 | 5-33.3 |

Currently, a typical site of electrode implantation for VNS therapy is at the cervical spinal level between the thyroid cartilage and the sternum of the patient. At this location, the vagus nerve is a single nerve fascicle containing a wide array of nerve fibers as summarized in Table 1. As a result, stimulation parameters used for VNS therapy are largely determined by titrating the various temporal properties of the electrical pulses (e.g., amplitude, frequency, duty cycle). Various studies applying VNS to animal models and human patients led to the establishment of recommended clinical parameters for antiepileptic and other applications of VNS. However, stimulation-evoked side effects, such as voice hoarseness, coughing, and pain, remain a problem in applying VNS therapy. These unwanted effects of VNS result from (1) the reversed recruitment order of myelinated nerve fibers during electrical stimulation (i.e., lower activation threshold for larger diameter fibers) and (2) the vast majority of larger diameter fibers within the vagus nerve innervate the voice box and upper airway via the RLN. Delivering electrical stimulation to the vagus nerve through bipolar nerve cuff electrode, for example, is known to result in non-selective activation of all nerve fibers within the nerve trunk, and hence little control over unintended generation of side-effects including unintended laryngeal activities.

The present method and system use one or more temporal parameters to minimize stimulation-evoked side effects, thereby maximizing the overall therapeutic efficacy of VNS. In this document, "temporal parameters" refer to parameters specifying timing of electrical stimulation pulses, such as pulse frequency and duty cycle. In various embodiments, electrical stimulation is delivered to a portion of a vagus nerve of a patient with one or more temporal parameters selected to modulate a cardiovascular function of the patient without evoking unwanted physiological responses. Such physiological responses include various functions of the patient that are modulated by the vagus nerve but not among the intended results of the electrical stimulation. In one embodiment, as discussed in this document as an example of the present method and system, electrical stimulation is delivered to a cervical or thoracic portion of the vagus nerve of a patient with the stimulation duty cycle selected to modulate a cardiovascular function of the patient without evoking unwanted laryngeal activities.

FIG. 1 is an illustration of an embodiment of a VNS system 100 and portions of an environment in which system 100 is used. FIG. 1 shows a portion of a vagus nerve 101 having segments or branches including a vagus nerve 102 and an RLN 106. A stimulation electrode 136 is placed on vagus nerve 102 to allow for delivery of VNS to modulate functions of thoracic organs, including a heart 105, and/or abdominal organs that are innervated by various branches of vagus nerve 101. In the illustrated embodiment, stimulation electrode 136 is placed on the cervical vagus nerve (the portion of vagus nerve 102 cranial to where RLN 106 branches out). In another embodiment, stimulation electrode 136 is placed on the thoracic vagus nerve (the portion of vagus nerve 102 caudal to where RLN 106 branches out). RLN 106 innervates laryngeal muscles (represented by a laryngeal muscle 107), whose activation by the VNS delivered through electrode 136 is typically considered an unwanted side effect. To provide a patient with therapeutic effects such as an improved cardiovascular function, VNS is delivered to vagus nerve 102 with one or more temporal stimulation parameters selected to modulate the cardiovascular function without causing contraction of laryngeal muscle 107. In one embodiment, the one or more temporal stimulation parameters include a duty cycle.

While the application involving vagus nerve 102, RLN 106, and laryngeal muscle 107 as illustrated in FIG. 1 is discussed as a specific example in this document, the present method may apply to other branches of the vagus nerve or other nerves being targets of neurostimulation. In various embodiments, one or more temporal stimulation parameters are selected for selective activation of target organs innervated by a nerve to which electrical stimulation is delivered.

In the illustrated embodiment, system 100 includes an implantable medical device 110 electrically coupled to electrode 136 through an implantable lead 130. Implantable medical device 110 includes a neurostimulator 120 encapsulated by an implantable housing 112, and a header 114 attached to implantable housing 112 and providing for connection to lead 130. Neurostimulator 120 is discussed below with reference to FIG. 2. In one embodiment, implantable medical device 110 is a neurostimulator. In other embodiments, in addition to neurostimulator 120, implantable medical device 110 includes one or more of a cardiac pacemaker, a cardioverter/defibrillator, a drug delivery device, a biologic therapy device, and any other monitoring or therapeutic devices. Lead 130 includes a proximal end 132, a distal end 133, and an elongate body 131 coupled between proximal end 132 and distal end 133. Proximal end 132 is configured to be connected to implantable medical device 110. Distal end 133 includes, or is otherwise coupled to, stimulation electrode 136. Stimulation electrode 136 is bipolar nerve cuff electrode. In various other embodiments, stimulation electrodes 136 includes any form of electrode that allows for activation of vagus nerve 102 by electrical stimulation delivered from neurostimulator 120.

Figure 2:
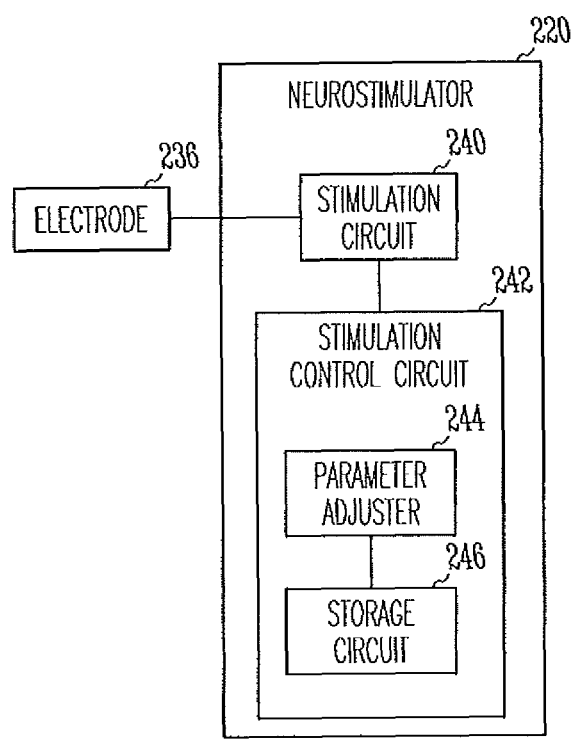
FIG. 2 is a block diagram illustrating an embodiment of an electrode and a neurostimulator of the VNS system.

FIG. 2 is a block diagram illustrating an embodiment of an electrode 236 and a neurostimulator 220. Electrode 236 represents an embodiment of stimulation electrode 136. Neurostimulator 220 represents an embodiment of neurostimulator 120.

Neurostimulator 220 includes a stimulation circuit 240 and a stimulation control circuit 242. Stimulation circuit 240 produces electrical stimulation pulses and delivers the electrical stimulation pulses to electrode 236. Stimulation control circuit 242 controls the delivery of the electrical stimulation pulses using a plurality of stimulation parameters and includes a parameter adjuster 244 and a storage circuit 246. Parameter adjuster 244 allows for adjustment of one or more temporal parameters of the plurality of stimulation parameters for selective activation or modulation of physiological functions controlled by the vagus nerve. In one embodiment, the plurality of stimulation parameters includes pulse amplitude, pulse width, pulse frequency, duty cycle, cycle unit, and stimulation duration. The pulse amplitude is the amplitude of each electrical stimulation pulse specified as voltage (e.g., for constant-voltage pulse) or current (e.g., for constant-current pulse). The pulse width is the duration of each electrical stimulation pulse. The pulse frequency is the frequency at which the electrical stimulation pulses are delivered and may also be specified as an inter-pulse interval being the time interval between successive pulses. The duty cycle is the ratio of a stimulation interval during which the electrical stimulation pulses are delivered to the cycle unit. The stimulation duration is the duration of a delivery of neurostimulation therapy. The cycle unit and the stimulation durations may be specified by time or number of pulses, and the duty cycles may be specified by time or number of pulses in each cycle unit. For example, "pulses delivered at a pulse frequency of 20 Hz at a duty cycle of 10% and a unit cycle of 1 second" is equivalent to "pulses delivered at a pulse frequency of 20 Hz at a duty cycle of 2 pulses per unit cycle of 20 pulses".

Storage circuit 246 stores values for the plurality of stimulation parameters including one or more values of one or more stimulation parameters selected to modulate one or more target physiological functions without substantially affecting one or more non-target physiological functions. In one embodiment, storage circuit 246 stores one or more values of one or more stimulation parameters selected to modulate a cardiovascular function without causing contraction of a laryngeal muscle. In one embodiment, a value of the duty cycle is selected to modulate a physiological function without substantially affecting another physiological function, and stored in storage circuit 246.

In various embodiments, the circuit of neurostimulator 220, including its various elements discussed in this document, is implemented using a combination of hardware and software. In various embodiments, stimulation control circuit 242 may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 3:
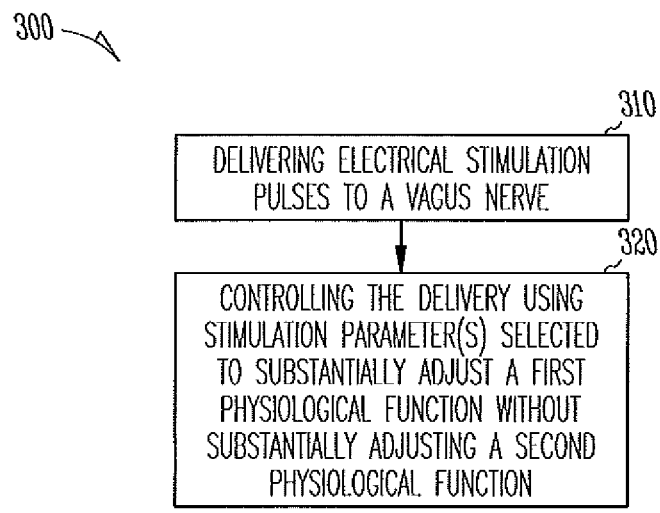
FIG. 3 is a flow chart illustrating an embodiment of a method for selective VNS using selected temporal parameter(s).

FIG. 3 is a flow chart illustrating an embodiment of a method 300 for selective VNS using selected one or more temporal parameters. In one embodiment, method 300 is performed using system 100 including its embodiments discussed in this document.

At 310, electrical stimulation pulses are delivered to a vagus nerve. In one embodiment, the electrical stimulation pulses are delivered to the vagus nerve through a stimulation electrode, such as a bipolar nerve cuff electrode, placed on the vagus nerve. In one embodiment, the electrical stimulation pulses are delivered from an implantable medical device connected to an implantable lead including, or otherwise electrically connected to, the stimulation electrode.

At 320, the delivery of the electrical stimulation pulses is controlled using one or more stimulation parameters selected to substantially adjust a first physiological function without substantially adjusting a second physiological function in a patient. In one embodiment, a temporal parameter, such as a duty cycle, is used to control the delivery of the electrical stimulation pulses for substantially adjusting the first physiological function without substantially adjusting the second physiological function. The second physiological function represents one or more physiological functions modulated by the vagus nerve but considered unwanted side effects of VNS in various embodiments.

In one embodiment, the value of the temporal parameter is determined by monitoring the effect of the delivery of the electrical stimulation pulses on the first and second physiological functions. A first physiological signal indicative of the first physiological function is sensed, and a first parameter indicative of the first physiological function is produced using the first physiological signal. A second physiological signal indicative of the second physiological function is sensed, and a second parameter indicative of the second physiological function is produced using the second physiological signal. The value of the temporal parameter is determined using the first parameter and the second parameter. In one embodiment, the temporal parameter is adjusted to determine a value that results in the first parameter being within a first threshold range and the second parameter being within a second threshold range. In one embodiment, a first base value of the first parameter is produced using the first physiological signal sensed while none of the electrical stimulation pulses is being delivered. A second base value of the second parameter is produced using the second physiological signal sensed while none of the electrical stimulation pulses is being delivered. One or more first stimulated values of the first parameter are produced each using the first physiological signal sensed while the electrical stimulation pulses are delivered with one of one or more values of the temporal parameter. One or more second stimulated values of the second parameter are produced each using the second physiological signal sensed while the electrical stimulation pulses are delivered with the one of the one or more values of the temporal parameter. The value of the temporal parameter is determined using the first base value, the second base value, the one or more first stimulated values, and the one or more second stimulated values.

In another embodiment, the value of the temporal parameter is determined by monitoring and using the effect of the delivery of the electrical stimulation pulses on the second physiological function, without monitoring or using the effect of the delivery of the electrical stimulation pulses on the first physiological function. The second physiological signal indicative of the second physiological function is sensed, and the second parameter indicative of the second physiological function is produced using the second physiological signal. The value of the temporal parameter is determined using the second parameter. In one embodiment, the temporal parameter is adjusted to determine the value that results in the second parameter being within a second threshold range. In one embodiment, the second base value of the second parameter is produced using the second physiological signal sensed while none of the electrical stimulation pulses is being delivered. One or more second stimulated values of the second parameter are produced each using the second physiological signal sensed while the electrical stimulation pulses are delivered with the one of the one or more values of the temporal parameter. The value of the temporal parameter is determined using the second base value and the one or more second stimulated values.

Figure 4:
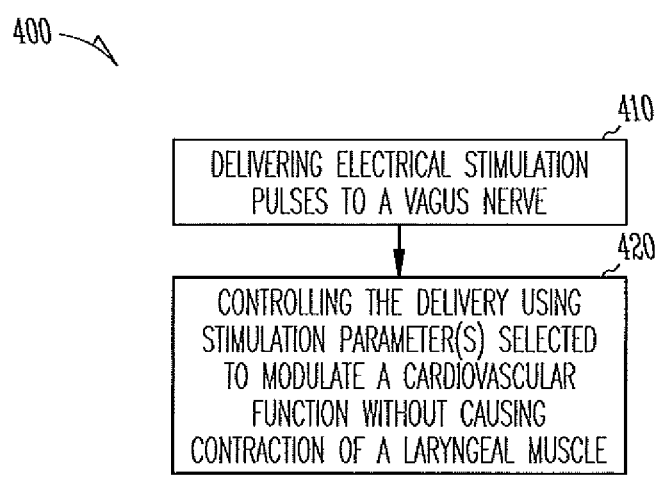
FIG. 4 is a flow chart illustrating another embodiment of a method for selective VNS using selected temporal parameter(s).

FIG. 4 is a flow chart illustrating an embodiment of a method 400 for selective VNS using selected one or more temporal parameters. Method 400 is an embodiment of method 300 with the first physiological function being a cardiovascular function and the second physiological function including contraction of a laryngeal muscle. In one embodiment, method 400 is performed using system 100 including its embodiments discussed in this document.

At 410, electrical stimulation pulses are delivered to a vagus nerve to modulate the cardiovascular function. In one embodiment, the electrical stimulation pulses are delivered to the vagus nerve through a stimulation electrode, such as a bipolar nerve cuff electrode, placed on the vagus nerve. In one embodiment, the electrical stimulation pulses are delivered from an implantable medical device connected an implantable lead including, or otherwise electrically connected to, the stimulation electrode.

At 420, the delivery of the electrical stimulation pulses is controlled using one or more stimulation parameters selected to modulate the cardiovascular function without causing contraction of the laryngeal muscle. In one embodiment, a temporal parameter, such as a duty cycle, is used to control the delivery of the electrical stimulation pulses for modulating the cardiovascular function without causing contraction of the laryngeal muscle.

Contraction of the laryngeal muscle is discussed as a specific example of an unwanted side effect of the delivery of the electrical stimulation pulses to the vagus nerve. In various embodiments, the delivery of the electrical stimulation pulses is controlled using one or more stimulation parameters selected to modulate the cardiovascular function without causing one or more physiological functions each considered an unwanted side effect.

In one embodiment, the value of the temporal parameter is determined by monitoring the effect of the delivery of the electrical stimulation pulses on the cardiovascular function and contraction of the laryngeal muscle. A first physiological signal indicative of the cardiovascular function is sensed, and a first parameter indicative of the cardiovascular function is produced using the first physiological signal. A second physiological signal indicative of contraction of the laryngeal muscle is sensed, and a second parameter indicative of contraction of the laryngeal muscle is produced using the second physiological signal. The value of the temporal parameter is determined using the first parameter and the second parameter. In one embodiment, the temporal parameter is adjusted to determine a value that results in the first parameter being within a first threshold range and the second parameter being within a second threshold range.

In another embodiment, the value of the temporal parameter is determined by monitoring and using the effect of the delivery of the electrical stimulation pulses on the contraction of the laryngeal muscle, without monitoring or using the effect of the delivery of the electrical stimulation pulses on the cardiovascular function. The second physiological signal indicative of contraction of the laryngeal muscle is sensed, and the second parameter indicative of contraction of the laryngeal muscle is produced using the second physiological signal. The value of the temporal parameter is determined using the second parameter. In one embodiment, the temporal parameter is adjusted to determine a value that results in the second parameter being within a second threshold range.

In an embodiment in which the effect of the delivery of the electrical stimulation pulses on the cardiovascular function is monitored and used, the first physiological signal includes an electrocardiographic (ECG) signal, and the first parameter includes a heart rate (in beats per minute, bpm). In various embodiments, the first physiological signal may also include an arterial blood pressure signal and/or a left ventricular (LV) blood pressure signal, and the first parameter may also include mean blood pressure (in mmHg) produced using the arterial blood pressure signal and/or LV contractility (rate of LV blood pressure change in mmHg/min) produced using the LV blood pressure signal. In one embodiment, the second physiological signal includes an electromyographic (EMG) signal sensed from a laryngeal muscle such as the posterior cricothyroid muscle, and the second parameter includes the amplitude of the EMG signal (in mV). In various embodiments, the second physiological signal may also include a signal indicative of movement of the laryngeal muscle, such an acceleration signal sensed by an accelerometer placed in or over the laryngeal muscle, and the first parameter may also include the amplitude of the signal, such as the amplitude of the acceleration signal.

In one embodiment, the temporal parameter is adjusted to determine a value that results in a change in the heart rate by a specified margin without increasing the amplitude of the EMG by a specified amount. In various other embodiments, the temporal parameter is further adjusted to determine a value that also results in a change in the blood pressure by a specified margin and/or a change in a measure of the cardiac contractility by a specified margin, without increasing the amplitude of the EMG by the specified amount. In one embodiment, a base value of the heart rate is produced using the ECG signal sensed while none of the electrical stimulation pulses is being delivered. A base value of the amplitude of the EMG signal is produced using the EMG signal sensed while none of the electrical stimulation pulses is being delivered. One or more stimulated values of the heart rate are produced each using the ECG signal sensed while the electrical stimulation pulses are delivered with one of one or more values of the temporal parameter. One or more stimulated values of the amplitude of the EMG are produced each using the EMG signal sensed while the electrical stimulation pulses are delivered with the one of the one or more values of the temporal parameter. The value of the temporal parameter is determined using the base value of the heart rate, the base value of the amplitude of the EMG signal, the one or more stimulated values of the heart rate, and the one or more stimulated values of the amplitude of the EMG signal.

In another embodiment, the temporal parameter is adjusted to determine a value that does not cause an increase in the amplitude of the EMG or the acceleration signal by a specified amount. In one embodiment, the base value of the amplitude of the EMG signal or the acceleration signal is produced using the EMG signal or the acceleration signal, respectively, sensed while none of the electrical stimulation pulses is being delivered. One or more stimulated values of the amplitude of the EMG or the acceleration signal are produced each using the EMG signal or the acceleration signal, respectively, sensed while the electrical stimulation pulses are delivered with the one of the one or more values of the temporal parameter. The value of the temporal parameter is determined using the base value of the amplitude of the EMG signal or the acceleration signal and the one or more stimulated values of the amplitude of the EMG signal or the acceleration signal.

Figure 5:
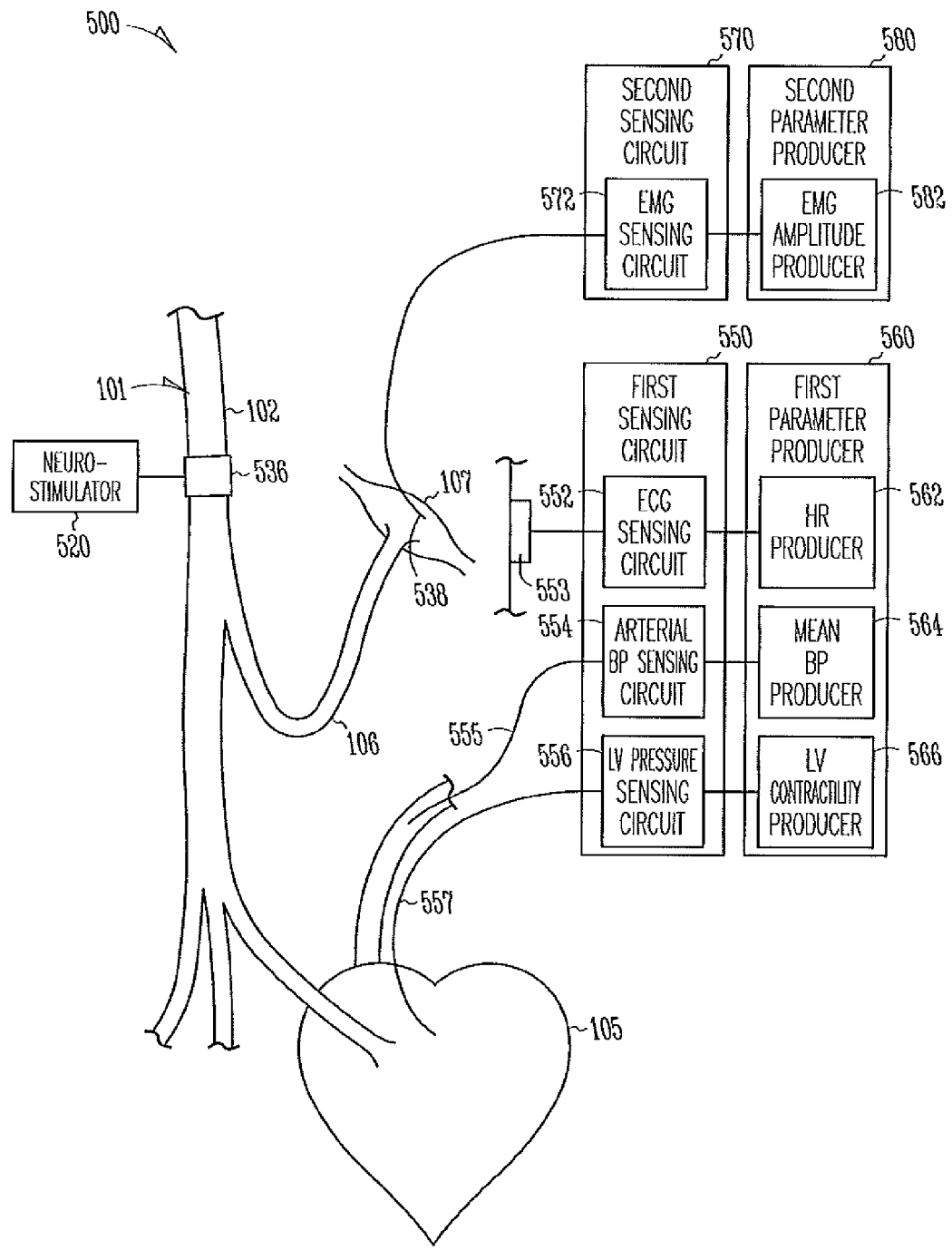
FIG. 5 is an illustration of a system for testing the method of FIG. 4.

FIG. 5 is an illustration of a system 500 for testing method 400. A bipolar helical nerve cuff electrode 536 is placed on vagus nerve 102 to test the feasibility of modulating a cardiovascular function without causing undesirable contraction of the laryngeal muscle by selecting a duty cycle of the VNS.

A neurostimulator 520 is electrically connected to electrode 536 to deliver electrical stimulation pulses to vagus nerve 102. An example for neurostimulator 520 is neurostimulator 220 as discussed above. Neurostimulator 520 may be an implantable device or an external device that is electrically coupled to the corresponding electrode via an implantable or percutaneous lead.

A first sensing circuit 550 senses a first physiological signal indicative of a cardiovascular function. A first parameter producer 560 produces a first parameter indicative of the cardiovascular function using the first physiological signal. As illustrated in FIG. 5, first sensing circuit 550 includes an ECG sensing circuit 552, an arterial blood pressure (BP) sensing circuit 554, and an LV pressure sensing circuit 556. First parameter producer 560 includes a heart rate (HR) producer 562, a mean BP producer 564, and an LV contractility producer 566. ECG sensing circuit 552 senses an ECG signal using surface electrodes 553. HR producer 562 produces a heart rate using the ECG signal. Arterial BP sensing circuit 554 senses an arterial blood pressure signal using an intravascular pressure sensing catheter 555. Mean BP producer 564 produces a mean arterial BP using the arterial blood pressure signal. LV pressure sensing circuit 556 senses an LV blood pressure signal using an intravascular pressure sensing catheter 557. LV contractility producer 566 produces a rate of LV pressure change being a measure of the LV contractility. In various embodiments, first sensing circuit 550 includes any one or more of ECG sensing circuit 552, arterial BP sensing circuit 554, LV pressure sensing circuit 556, and other sensing circuits that sense signals indicative of the cardiovascular function, depending on the nature of the cardiovascular function to be modulated and the measure or indication of that cardiovascular function selected to be monitored. Likewise, first parameter producer 560 includes any one or more of HR producer 562, mean BP producer 564, LV contractility producer 566, and other parameter producers that produce parameters indicative of the cardiovascular function.

A second sensing circuit 570 senses a second physiological signal indicative of the contractions of the laryngeal muscle. A second parameter producer 580 produces a second parameter indicative of the contractions of the laryngeal muscle using the second physiological signal. As illustrated in FIG. 5, second sensing circuit 570 includes an EMG sensing circuit 572 that senses an EMG signal using an intramuscular electrode 538 inserted into laryngeal muscle 107 (e.g., posterior cricothyroid muscle). Second parameter producer 580 includes EMG amplitude producer 582 that produces an amplitude of the EMG signal using the EMG signal.

Figure 6:
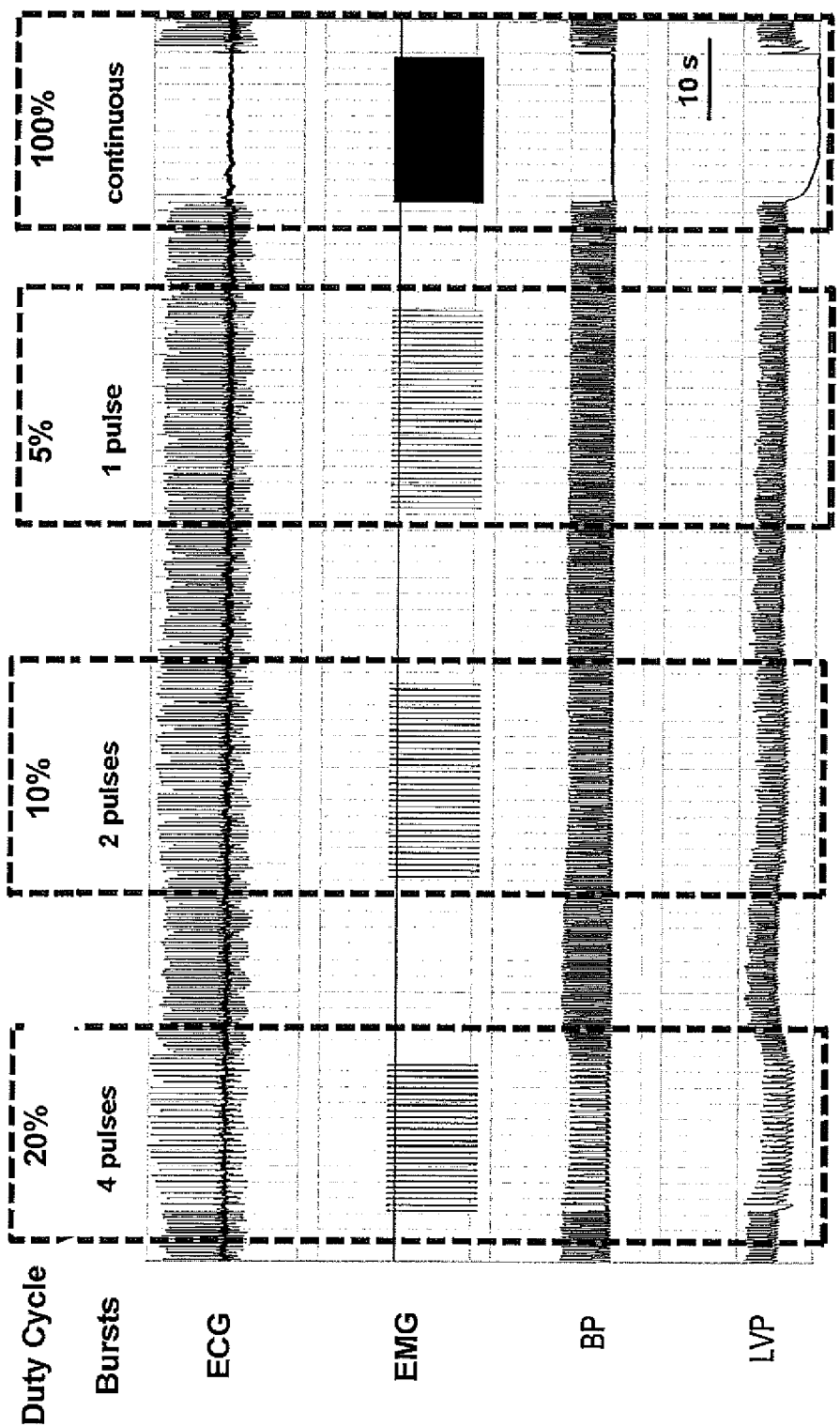
FIG. 6 is an illustration of results of testing the method of FIG. 4.

FIG. 6 is an illustration of results of testing the method 400. The feasibility of selectively modulating physiological functions by VNS with a selected temporal parameter was investigated using a canine model and system 500. FIG. 6 shows the ECG signal (ECG), the EMG signal (EMG), the arterial BP signal (BP), and the LV pressure signal (LVP) sensed during VNS with various duty cycles using system 500. Compared to a baseline, electrical stimulation pulses delivered to the cervical vagus nerve at a pulse amplitude of 3 mA, a pulse width of 300 μs, and a pulse frequency of 20 Hz evoked visible reductions in the ECG signal, the arterial BP signal, and the LV pressure signal. The magnitude of the reduction varied as a function of the duty cycle, which is labeled in FIG. 6 as both a percentage and the number of pulses per burst delivered per unit circle (1 second or 20 pulses). The results illustrated in FIG. 6 were quantified as parameters averaged over 20 seconds (20 unit cycles) in Table 2. The baseline values of the parameters are produced using signals sensed over 20 seconds prior to the delivery of the electrical stimulation pulses to the cervical vagus nerve. Table 2 indicates, for example, that at a 5% duty cycle, a 21% drop in the heart rate is achieved. When compared to the increase in the amplitude of the EMG signal during continuous stimulation (263% increase from the baseline), a remarkably smaller increase in the amplitude of the EMG signal is achieved during stimulation at the 5% duty cycle (47% increase from the baseline). It is noted that the changes in these parameters indicative of the cardiovascular functions are independent of the phase of the ECG, such as the Q-wave, at which the electrical stimulation pulses are delivered. This suggests that VNS may be delivered to modulate cardiovascular functions without the need of a sensor for monitoring timing of phases for each cardiac cycle of the patient.

TABLE 2

Summary of Parameters Averaged over 20 Seconds (20 Unit Cycles).

|  | Baseline | Continuous (100%) | 4 pulses (20%) | 2 pulses (10%) | 1 pulse (5%) |
| --- | --- | --- | --- | --- | --- |
| Heart Rate (bpm) | 111 | 0 | 60 | 85 | 88 |
| Amplitude of EMG Signal (mV) | 5.5 | 79.7 | 19.3 | 11.3 | 8.1 |
| Mean BP (mmHg) | 82 | 5 | 41 | 51 | 53 |
| LV Contractility (mmHg/min) | 34 ± 2 | 0 | 20 ± 3 | 25 ± 3 | 23 ± 3 |

In various embodiments, VNS is applied with a temporal parameter such as the duty cycle to substantially modulate a physiological function of a patient without substantially affecting another physiological function on the patient. A physiological function is substantially modulated when the stimulation-evoked change in this physiological function reaches or exceeds a specified threshold. A physiological function is not substantially affected when the stimulation-evoked change in this physiological function is below a specified threshold. In various embodiments, the temporal parameter is selected, for example, using parameters indicative of these physiological functions and thresholds representative of a balance point between effects on these physiological functions.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method or electrically stimulating a vagus nerve, the method comprising:
   delivering electrical stimulation pulses to the vagus nerve through an electrode placed on the vagus nerve; and
   controlling delivery of the electrical stimulation pulses using one or more temporal parameters selected to result in substantial change in a cardiovascular function without causing contraction of a laryngeal muscle, the one or more temporal parameters specifying timing of the electrical stimulation pulses, the cardiovascular function adjustable by the electrical stimulation pulses delivered to the vagus nerve through the electrode placed on the vagus nerve,
wherein controlling the delivery of the electrical stimulation pulses includes adjusting a duty cycle of the one or more temporal parameters such that a first parameter indicative of the cardiovascular function is within a first threshold range and a second parameter indicative of the contraction of the laryngeal muscle is within a second threshold range.

2. The method of claim 1, wherein delivering the electrical stimulation pulses to the vagus nerve comprises delivering the electrical stimulation pulses from an implantable medical device.

3. The method of claim 1, comprising using the duty cycle and a pulse frequency of the one or more temporal parameters selected to result in the substantial change in the cardiovascular function without causing contraction of the laryngeal muscle.

4. The method of claim 1, comprising:
sensing a second physiological signal indicative of contraction of the laryngeal muscle; and
determining the duty cycle using the second physiological signal.

5. The method of claim 4, further comprising sensing a first physiological signal indicative of the cardiovascular function, and wherein determining the duty cycle comprises determining the duty cycle using the first physiological signal and the second physiological signal.

6. The method of claim 5, wherein delivering the electrical stimulation pulses comprises delivering a train of bursts at a specified burst frequency, and determining the duty cycle comprises determining a number of pulses in each of the bursts.

7. The method of claim 5, wherein determining the duty cycle comprises:
producing a first parameter indicative of the cardiovascular function using the first physiological signal;
producing a second parameter indicative of the contraction of the laryngeal muscle using the second physiological signal; and
determining a value for the duty cycle using the first parameter and the second parameter.

8. The method of claim 7, wherein determining the value for the duty cycle comprises:
producing a first base value of the first parameter using the first physiological signal sensed while none of the electrical stimulation pulses is being delivered;
producing a second base value of the second parameter using the second physiological signal sensed while none of the electrical stimulation pulses is being delivered;
producing one or more first stimulated values of the first parameter each using the first physiological signal sensed while the electrical stimulation pulses are delivered;
producing one or more second stimulated values of the second parameter each using the second signal sensed while the electrical stimulation pulses are delivered; and
determining the value for the duty cycle using the first base value, the second base value, the one or more first stimulated values, and the one or more second stimulated values.

9. The method of claim 5, wherein sensing the first physiological signal comprises sensing an electrocardiographic (ECG) signal, and sensing the second physiological signal comprises sensing an electromyographic (EMG) signal from the laryngeal muscle.

10. The method of claim 9, comprising adjusting the duty cycle to change a heart rate by a specified margin without increasing the amplitude of the EMG by a specified amount.

11. The method of claim 9, wherein sensing the first physiological signal comprises sensing the ECG signal and an arterial blood pressure signal.

12. The method of claim 9, wherein sensing the first physiological signal co wises sensing the ECG signal and a left ventricular blood pressure signal.

13. The method of claim 9, wherein sensing the second physiological signal comprises sensing the EMG signal from the laryngeal muscle and an accelerometer signal indicative of movement of the laryngeal muscle.

14. The method of claim 5, wherein sensing the first physiological signal comprises sensing an arterial blood pressure signal, and sensing the second physiological signal comprises sensing an electromyographic (EMG) signal from the laryngeal muscle.

15. The method of claim 5, wherein sensing the first physiological signal comprises sensing a left ventricular blood pressure signal, and sensing the second physiological signal comprises sensing an electromyographic (EMG) signal from the laryngeal muscle.

16. The method of claim 1, wherein controlling the delivery of the electrical stimulation pulses comprises controlling delivery of the electrical stimulation pulses using the one or more temporal parameters selected to change a heart rate by a specified margin without causing contraction of the laryngeal muscle.

17. The method of claim 1, wherein controlling the delivery of the electrical stimulation pulses comprises controlling delivery of the electrical stimulation pulses using the one or more temporal parameters selected to change a blood pressure by a specified margin without causing contraction of the laryngeal muscle.

18. The method of claim 1, wherein controlling the delivery of the electrical stimulation pulses comprises controlling delivery of the electrical stimulation pulses using the one or more temporal parameters selected to change a measure of cardiac contractility by a specified margin without causing contraction of the laryngeal muscle.

19. The method of claim 1, wherein delivering electrical stimulation pulses comprises delivering the electrical stimulation pulses to the vagus nerve through the electrode placed on a cervical or thoracic portion of the vagus nerve.

* * * * *